United States Patent [19]
Iwasaki et al.

[11] Patent Number: 6,162,948
[45] Date of Patent: *Dec. 19, 2000

[54] NAPHTHALENEDICARBOXYLIC ACID PARTICLES AND PROCESS FOR THE PRODUCTION THEREOF

[75] Inventors: Hiroshi Iwasaki; Satoshi Inoki, both of Yamaguchi, Japan

[73] Assignee: Mitsui Chemicals Inc, Tokyo, Japan

[ * ] Notice: This patent is subject to a terminal disclaimer.

[21] Appl. No.: 09/091,795

[22] PCT Filed: May 14, 1997

[86] PCT No.: PCT/JP97/01619

§ 371 Date: Jun. 23, 1998

§ 102(e) Date: Jun. 23, 1998

[87] PCT Pub. No.: WO97/44307

PCT Pub. Date: Nov. 27, 1997

[30] Foreign Application Priority Data

May 20, 1996 [JP] Japan ..................................... 8-124836
Oct. 24, 1996 [JP] Japan ..................................... 8-282191

[51] Int. Cl.[7] .................................................... C07C 51/42
[52] U.S. Cl. ........................................... 562/486; 562/490
[58] Field of Search ...................................... 562/486, 490

[56] References Cited

U.S. PATENT DOCUMENTS 5,149,867  9/1992  Chen et al. ............................. 562/486
5,292,934  3/1994  Sikkenga et al. ....................... 562/413
5,872,284  2/1999  Iwasaki et al. ......................... 562/486

FOREIGN PATENT DOCUMENTS 6505512   6/1994  Japan .
WO9312065 6/1993  WIPO .

OTHER PUBLICATIONS

Database WPI, Section Ch, Week 7628, Derwent Publications Ltd., London, GB; Class A41, AN 76–53662X & SU 486 008 A (Monomers Res Inst), Jan. 15, 1976.

Primary Examiner—Porfirio Nazario-Gonzalez

[57] ABSTRACT

The present invention provides particles of naphthalenedicarboxylic acid (NDA) exhibiting excellent slurry fluidity, which have an EG slurry property value of 2.7 or below, the above EG slurry property value being defined as a molar ratio of ethylene glycol (EG) to NDA (moles of EG/moles of NDA) of a slurry composed of a mixture of NDA and EG, the above slurry having a viscosity of 1000 cP as measured by Brookfield viscometer. The use of the above naphthalenedicarboxylic acid particles as a raw material for the production of polyethylene naphthalate is advantageous not only from the economic point of view but also in scarcely forming reaction products which deteriorate the quality of polyethylene naphthalate.

13 Claims, No Drawings

NAPHTHALENEDICARBOXYLIC ACID PARTICLES AND PROCESS FOR THE PRODUCTION THEREOF

CROSS-REFERENCE TO RELATED APPLICATION

This application is the National Phase entry, 35 USC 371, of International PCT application, PCT/JP97/01619, filed May 14, 1997, and designating the United States.

FIELD OF THE INVENTION

The present invention relates to naphthalenedicarboxylic acid particles exhibiting excellent slurry fluidity and a process for producing the same.

BACKGROUND OF THE INVENTION

The polyethylene naphthalate is commonly produced by the process comprising reacting naphthalenedicarboxylic acid or an ester derivative thereof with ethylene glycol or an ester derivative thereof for esterification to thereby produce an ester of naphthalenedicarboxylic acid and ethylene glycol and carrying out a polycondensation of the above ester of naphthalenedicarboxylic acid and ethylene glycol in the presence of a polycondensation catalyst. In this process for producing the polyethylene naphthalate, a slurry containing naphthalenedicarboxylic acid and ethylene glycol (NDA/EG slurry) is continuously fed to the esterification step. This NDA/EG slurry is required to have excellent fluidity from the viewpoint of, for example, easiness in operation.

The particle sizes of commercially available naphthalenedicarboxylic acid are generally tens of microns, and the particle sizes are so uniform that the fluidity of the NDA/EG slurry is not always good. There is a method of improving the fluidity of the NDA/EG slurry, which comprises regulating the particle sizes of naphthalenedicarboxylic acid. However, the naphthalenedicarboxylic acid exhibits low solubility in most solvents, so that regulating the particle sizes of naphthalenedicarboxylic acid is difficult.

With respect to the method of regulating the particle sizes of naphthalenedicarboxylic acid, for example, Published Japanese Translation of PCT Patent Applications from Other States, No. 505512/1994 describes a process for producing naphthalene-2,6-dicarboxylic acid, which comprises the steps of:

hydrolyzing a dialkyl naphthalene-2,6-dicarboxylate by water at a reaction temperature of at least about 450° F. (232° C.) under liquid phase condition for a period of time sufficient for converting most of the dialkyl naphthalene-2,6-dicarboxylate to naphthalene-2,6-dicarboxylic acid to thereby obtain a reaction product mixture, the above water being present in an amount sufficient for dissolving at least about 10% by weight of formed naphthalene-2,6-dicarboxylic acid at the above reaction temperature (step a); and recovering the naphthalene-2,6-dicarboxylic acid from the reaction product mixture (step b). In this process, as described in Example 10, the Brookfield viscosity is 800 cP when the molar ratio of EG/NDA is 3, and the Brookfield viscosity is 2430 cP when the molar ratio of EG/NDA is 2.5. Thus, the molar ratio of EG/NDA exhibited when the Brookfield viscosity is 1000 is about 2.9. The naphthalenedicarboxylic acid exhibiting a molar ratio of EG/NDA of about 3 when the Brookfield viscosity is 1000 cP is known as the naphthalenedicarboxylic acid with the highest fluidity.

Of course, when increasing the ratio of ethylene glycol in the NDA/EG slurry, the fluidity of the NDA/EG slurry is improved. However, the increase of the ratio of ethylene glycol is disadvantageous not only from the economic point of view but also in that the probability of formation of reaction products which deteriorate the quality of polyethylene naphthalate is increased.

In the above circumstances, there is a demand for the development of naphthalenedicarboxylic acid particles which can produce an NDA/EG slurry having a low viscosity and the development of a process for producing such naphthalenedicarboxylic acid particles.

The present invention has been made taking the above current situation into account. The object of the present invention is to provide naphthalenedicarboxylic acid particles which exhibit excellent slurry fluidity when formed together with ethylene glycol into a slurry.

SUMMARY OF THE INVENTION

One form of naphthalenedicarboxylic acid particles according to the present invention have an EG slurry property value of 2.7 or below, the above EG slurry property value being defined as a molar ratio of ethylene glycol to naphthalenedicarboxylic acid (moles of ethylene glycol/moles of naphthalenedicarboxylic acid) of a slurry comprising a mixture of naphthalenedicarboxylic acid and ethylene glycol, the above slurry having a viscosity of 1000 cP as measured by Brookfield viscometer.

Another form of naphthalenedicarboxylic acid particles according to the present invention comprises naphthalenedicarboxylic acid particles whose particle size is greater than 100 $\mu$m but smaller than 300 $\mu$m in a ratio of at least 50% by weight.

A further form of naphthalenedicarboxylic acid particles according to the present invention comprises naphthalenedicarboxylic acid particles whose particle size is greater than 100 $\mu$m but smaller than 300 $\mu$m in a ratio of at least 50% by weight and naphthalenedicarboxylic acid particles whose particle size is smaller than 38 $\mu$m in a ratio of at least 20% by weight.

Still a further form of naphthalenedicarboxylic acid particles according to the present invention has an EG slurry property value of 2.7 or below, the above naphthalenedicarboxylic acid particles comprising naphthalenedicarboxylic acid particles whose particle size is greater than 100 $\mu$m but smaller than 300 $\mu$m in a ratio of at least 50% by weight.

Still a further form of naphthalenedicarboxylic acid particles according to the present invention has an EG slurry property value of 2.7 or below, the above naphthalenedicarboxylic acid particles comprising naphthalenedicarboxylic acid particles whose particle size is greater than 100 $\mu$m but smaller than 300 $\mu$m in a ratio of at least 50% by weight and naphthalenedicarboxylic acid particles whose particle size is smaller than 38 $\mu$m in a ratio of at least 20% by weight.

The process for producing naphthalenedicarboxylic acid particles according to the present invention comprises the steps of:

heating a liquid mixture of naphthalenedicarboxylic acid and/or an ester of naphthalenedicarboxylic acid, an alcohol and water to thereby prepare a water/alcohol solution of predetermined alcohol concentration in which naphthalenedicarboxylic acid and an ester of naphthalenedicarboxylic acid are dissolved, and lowering the alcohol concentration of the water/alcohol solution to thereby hydrolyze the ester of naphthalenedicarboxylic acid contained in the water/alcohol solution, so that naphthalenedicarboxylic acid particles are precipitated and separated.

Naphthalenedicarboxylic acid particles which exhibit excellent slurry fluidity when formed together with ethylene glycol into a slurry can be obtained by the above process.

In the present invention, it is preferred that the liquid mixture of naphthalenedicarboxylic acid and/or an ester of naphthalenedicarboxylic acid, an alcohol and water contain the alcohol in a concentration ranging from 20 to 95% by weight based on the total of the alcohol and water. Further, in the present invention, it is preferred that the alcohol concentration of the water/alcohol solution be lowered so as to range from 0 to 20% by weight based on the total of the alcohol and water. Preferably, the alcohol concentration is maintained at 20% by weight or higher in the initial stage of the hydrolysis and, subsequently, is gradually lowered.

The above alcohol is preferred to be selected from among alcohols each having up to 8 carbon atoms. Examples of suitable alcohols include aliphatic alcohols such as methanol, ethanol, propanol, isopropanol, butanol, pentanol, hexanol, heptanol and octanol; alicyclic alcohols such as cyclohexanol; aromatic alcohols such as phenol and benzyl alcohol; and dialcohols such as ethylene glycol. Of these, methanol, ethanol and propanol are especially preferred.

In the present invention, it is preferred that the precipitated naphthalenedicarboxylic acid particles be subjected to a solid-liquid separation at 100° C. or higher. Naphthalenedicarboxylic acid particles having the above EG slurry property and/or particle size distribution can be obtained by the solid-liquid separation of the precipitated naphthalenedicarboxylic acid particles under the above condition.

BEST MODE OF THE INVENTION

The naphthalenedicarboxylic acid particles and process or producing naphthalenedicarboxylic acid particles according to the present invention will be described in greater detail below.

The naphthalenedicarboxylic acid particles according to the present invention exhibit excellent slurry fluidity and generally have an EG slurry property value of 2.7 or below, preferably, 2.5 or below, the above EG slurry property value being defined as a molar ratio of ethylene glycol (EG) to naphthalenedicarboxylic acid (NDA) (moles of EG/moles of NDA) of a slurry comprising a mixture of NDA and EG, the above slurry having a viscosity of 1000 cP as measured by Brookfield viscometer. The smaller the value of EG slurry property, the more excellent the fluidity of the NDA/EG slurry.

The naphthalenedicarboxylic acid particles of the present invention includes naphthalenedicarboxylic acid particles whose particle size is greater than 100 μm but smaller than 300 μm in a ratio of at least 50% by weight, preferably 55~80% by weight and, more preferably, 60~80% by weight, as measured by sifting with the use of a series of sieves whose respective openings are 500, 300, 212, 150, 100, 75, 53 and 38 μm. Further, the naphthalenedicarboxylic acid particles of the present invention includes naphthalenedicarboxylic acid particles whose particle size is greater than 100 μm but smaller than 300 μm in the above ratio and naphthalenedicarboxylic acid particles whose particle size is smaller than 38 μm in a ratio of at least 20% by weight, preferably 23~45% by weight and, more preferably 26~40% by weight.

In the present invention, the naphthalenedicarboxylic acid particles are preferred to be those having the above EG slurry property value and containing naphthalenedicarboxylic acid particles whose particle size is greater than 100 μm but smaller than 300 μm in the above ratio and are especially preferred to be those having the above EG slurry property value, containing naphthalenedicarboxylic acid particles whose particle size is greater than 100 μm but smaller than 300 μm in the above ratio and containing naphthalenedicarboxylic acid particles whose particle size is smaller than 38 μm in the above ratio.

An NDA/EG slurry having higher fluidity can be prepared with less amount of ethylene glycol from the naphthalenedicarboxylic acid particles of the present invention than from the conventional naphthalenedicarboxylic acid particles. Therefore, the use of the naphthalenedicarboxylic acid particles of the present invention as a raw material for the production of polyethylene naphthalate is advantageous not only from the economic point of view but also in scarcely forming reaction products which deteriorate the quality of polyethylene naphthalate.

The process for producing naphthalenedicarboxylic acid particles according to the present invention comprises the steps of:

heating a liquid mixture of naphthalenedicarboxylic acid and/or an ester of naphthalenedicarboxylic acid, an alcohol and water to thereby prepare a water/alcohol solution of predetermined alcohol concentration in which naphthalenedicarboxylic acid and an ester of naphthalenedicarboxylic acid are dissolved, and lowering the alcohol concentration of the water/alcohol solution to thereby hydrolyze the ester of naphthalenedicarboxylic acid contained in the water/alcohol solution, so that naphthalenedicarboxylic acid particles are precipitated and separated.

In the first step of the present invention, a liquid mixture is prepared by mixing together naphthalenedicarboxylic acid and/or an ester of naphthalenedicarboxylic acid, an alcohol and water.

In this step, naphthalenedicarboxylic acid and/or an ester of naphthalenedicarboxylic acid are/is used in an amount of 0.007 to 0.5 mol, preferably, 0.03 to 0.10 mol per mol of the alcohol. The alcohol is generally used in an amount of 20 to 95% by weight, preferably 40 to 90% by weight and, more preferably 60 to 80% by weight based on the total of the alcohol and water of the liquid mixture.

In the present invention, subsequently, the above liquid mixture is heated at 100 to 300° C., preferably, 160 to 280° C. This heating of the liquid mixture is conducted under a pressure of 2 to 80 kg/cm$^2$, preferably, 10 to 50 kg/cm$^2$ for a period of 0.2 to 6 hr, preferably, 1 to 4 hr.

The above heating of the liquid mixture esterifies part of the naphthalenedicarboxylic acid to thereby form an ester of naphthalenedicarboxylic acid (naphthalenedicarboxylic monoester and naphthalenedicarboxylic diester), so that the solubility of the naphthalenedicarboxylic acid in the water/alcohol solution is increased. As a result, there is obtained a water/alcohol solution (aqueous alcohol solution) in which the naphthalenedicarboxylic acid and the ester of naphthalenedicarboxylic acid are dissolved is obtained.

When an ester of naphthalenedicarboxylic acid (naphthalenedicarboxylic monoester and/or naphthalenedicarboxylic diester) is used as a raw material, part of the ester of naphthalenedicarboxylic acid is hydrolyzed to thereby form naphthalenedicarboxylic acid, so that there is obtained a water/alcohol solution in which the naphthalenedicarboxylic acid and the ester of naphthalenedicarboxylic acid are dissolved is obtained.

The above heating of the liquid mixture can be conducted in an atmosphere of inert gas such as nitrogen gas.

In the present invention, thereafter, the alcohol concentration of the water/alcohol solution in which the naphthalenedicarboxylic acid and the ester of naphthalenedicarboxylic acid are dissolved is lowered to thereby hydrolyze the ester of naphthalenedicarboxylic acid. The thus obtained crystal particles of naphthalenedicarboxylic acid are precipitated, separated and recovered.

Although the method of lowering the alcohol concentration of the water/alcohol solution is not particularly limited, the lowering of the alcohol concentration can be accomplished by, for example, the method in which water is added to the water/alcohol solution, the method in which at least part of the alcohol is evaporated from the water/alcohol solution, the method in which a water/alcohol solution having an alcohol concentration lower than that of the above water/alcohol solution is added to the above water/alcohol solution or the method being a combination of the above methods, e.g., the method in which water is added to the water/alcohol solution, followed by evaporation of part of the alcohol.

Preferably, the alcohol concentration is maintained at 20% by weight or higher in the initial stage of the hydrolysis and, subsequently, is gradually lowered. The final lowering of the alcohol concentration of the water/alcohol solution is conducted so that the alcohol concentration generally becomes 0 to 20% by weight, preferably 0 to 5% by weight and, more preferably 0 to 3% by weight based on the total of the alcohol and water.

The hydrolysis of the ester of naphthalenedicarboxylic acid is generally conducted at 100 to 300° C., preferably, 160 to 280° C. for a period of 0.2 to 6 hr, preferably, 1 to 4 hr under a pressure of 2 to 80 kg/cm$^2$, preferably, 10 to 50 kg/cm$^2$. In the middle of the hydrolysis, the temperature can be decreased to a level at which crystals precipitate.

The hydrolysis can be conducted in the co-presence of carbon dioxide. The co-presence of carbon dioxide enables shifting the equilibrium of ester of naphthalenedicarboxylic acid and naphthalenedicarboxylic acid toward the side of naphthalenedicarboxylic acid, so that the recovery of naphthalenedicarboxylic acid can be increased.

After the completion of the hydrolysis, formed naphthalenedicarboxylic acid particles can be precipitated in crystal form by cooling the water/alcohol solution. Separation of precipitated naphthalenedicarboxylic acid particles from the water/alcohol solution gives naphthalenedicarboxylic acid particles having a broad particle size distribution. The particle size distribution of naphthalenedicarboxylic acid particles can be regulated by, for example, controlling the change of the alcohol concentration of the water/alcohol solution subjected to the hydrolysis.

The thus obtained naphthalenedicarboxylic acid particles generally have an EG slurry property value of 4 or below, preferably, 3.5 or below.

Subjecting the naphthalenedicarboxylic acid precipitated after the hydrolysis to a solid-liquid separation conducted at 100° C. or higher, preferably, 120 to 250° C. produces:

naphthalenedicarboxylic acid particles generally having an EG slurry property value of 2.7 or below, preferably, 2.5 or below;

naphthalenedicarboxylic acid particles which comprise naphthalenedicarboxylic acid particles whose particle size is greater than 100 μm but smaller than 300 μm in a ratio of at least 50% by weight, preferably 55~80% by weight and, more preferably 60~80% by weight;

naphthalenedicarboxylic acid particles which comprise naphthalenedicarboxylic acid particles whose particle size is greater than 100 μm but smaller than 300 μm in the above ratio and whose particle size is smaller than 38 μm in a ratio of at least 20% by weight, preferably 23~45% by weight and, more preferably 26 40% by weight;

naphthalenedicarboxylic acid particles having the above EG slurry property value and comprising naphthalenedicarboxylic acid particles whose particle size is greater than 100 μm but smaller than 300 μm in the above ratio; and naphthalenedicarboxylic acid particles having the above EG slurry property value, comprising naphthalenedicarboxylic acid particles whose particle size is greater than 100 μm but smaller than 300 μm in the above ratio and whose particle size is smaller than 38 μm in the above ratio.

An NDA/EG slurry having higher fluidity can be prepared with less amount of ethylene glycol from the naphthalenedicarboxylic acid particles obtained by the process of the present invention than from the conventional naphthalenedicarboxylic acid particles. Therefore, the use of the naphthalenedicarboxylic acid particles of the present invention as a raw material for the production of polyethylene naphthalate is advantageous not only from the economic point of view but also in scarcely forming reaction products which deteriorate the quality of polyethylene naphthalate.

EFFECT OF THE INVENTION

The naphthalenedicarboxylic acid particles of the present invention are excellent in slurry fluidity.

The naphthalenedicarboxylic acid particles which are excellent in slurry fluidity can be obtained by the process of the present invention.

EXAMPLE

The present invention will now be illustrated in greater detail with reference to the following Examples, which in no way limit the scope of the invention.

Example 1

120 g of raw material NDA, 240 g of methanol and 160 g of water were charged into a 1000 ml autoclave equipped with a distillation column, and the inside of the reaction system was purged with nitrogen (pressurized to 10 kg/cm$^2$ with nitrogen). The contents of the autoclave were heated at 245° C. for 2 hr.

Subsequently, the internal pressure of the autoclave was gradually reduced and, while feeding 250 g of water over a period of 3 hr, 235 g of methanol was distilled off from the top of the distillation column provided on the autoclave. In this experiment, the methanol withdrawing rate was substantially constant.

Then, the autoclave was cooled to 150° C. and crystals were separated from the liquid at this temperature. The crystals were washed with 1000 ml of water at 150° C. and the autoclave was further cooled to 25° C. Thus, 96 g of NDA was recovered. The particle size distribution of the obtained NDA is given in Table 1.

The obtained NDA had its particle sizes broadly distributed from "150 μm on" to "53 μm on" and the EG slurry property thereof was as excellent as 2.5.

206 g of the NDA obtained by the above procedure and 155 g of EG were charged into a glass flask provided with a simple distilling equipment, put on an 80° C. oil bath and heated to 225° C. over a period of 30 min. The heating was continued at that temperature. During the heating, distillate water flowing from the top of the distillation column was recovered. The time at which the distillation of water formed as a result of the advance of the esterification was no longer observed was regarded as the completion of the esterification.

21 mg of germanium dioxide as a polymerization catalyst, and 15 mg of tetraethylammonium hydroxide and 39 mg of phosphoric acid as stabilizers were dissolved in 5 g of EG and added to the above product of esterification of NDA. The product of esterification of NDA having, added thereto, the polymerization catalyst and the stabilizers was heated to 260° C. and agitated for 1 hr while recovering distillate EG. The pressure of the reaction system was reduced to 1 Torr or below while raising the temperature thereof to 280° C. over a period of 1 hr, thereby distilling EG. The reaction was further continued for 1.5 hr at 280° C. under a reduced pressure of 1 Torr or below while distilling EG. Then, the reaction was terminated, and formed polyethylene naphthalate was recovered.

The thus recovered polyethylene naphthalate had an intrinsic viscosity of 0.55 dl/g (dissolved in a solution composed of a 1:1 mixture of o-chlorophenol and phenol and measured at 25° C.), a glass transition temperature (Tg) of 111° C. as measured by a differential scanning calorimeter (DSC) and a melting point (Tm) of 256° C.

TABLE 1

|  |  | Raw material NDA | Example 1 |
|---|---|---|---|
| Particle | 500 µm on | 0.3 | 0.1 |
| size | 300 µm on | 0.1 | 0.2 |
| distri- | 212 µm on | 0.1 | 7.3 |
| bution | 150 µm on | 0.1 | 28.6 |
| (wt %) | 100 µm on | 0.2 | 25.1 |
|  | 75 µm on | 0.1 | 5.5 |
|  | 53 µm on | 0.1 | 2.2 |
|  | 38 µm on | 0.1 | 2.4 |
|  | 38 µm pass | 98.9 | 28.7 |
| EG slurry property (EG(mol)/NDA(mol)) |  | 7 | 2.5 | on: particles did not pass through the sieve with the indicated opening and remained on the sieve.
pass: particles passed through the sieve with the indicated opening.

Example 2

100 g of naphthalene-2,6-dicarboxylic acid having a particle size distribution specified in Table 2 (hereinafter referred to as "raw material NDA"), 240 g of methanol and 160 g of water were charged into a 1000 ml autoclave equipped with a distillation column, and the inside of the reaction system was purged with nitrogen (pressurized to 10 kg/cm² with nitrogen). The contents of the autoclave were heated at 245° C. for 2 hr.

Subsequently, the internal pressure of the autoclave was gradually reduced and, while feeding 250 g of water over a period of 3 hr, 220 g of methanol was distilled off from the top of the distillation column provided on the autoclave. In this experiment, about 200 g of unreacted methanol was first withdrawn over a period of 20 min and, thereafter, the remaining methanol was slowly withdrawn.

Then, the autoclave was cooled to 25° C. and crystals were separated from the liquid. Thus, 98 g of NDA was recovered. The particle size distribution of the obtained NDA is given in Table 2.

The particle size of NDA increased from the "predominantly 38 µm pass" of the raw material NDA to "150 µm on to 53 µm on" of the product NDA. Further, the product NDA had its particle size distribution broadened and the EG slurry property thereof was as good as 3.2 as compared with those of the raw material NDA.

Example 3

113 g of raw material NDA, 240 g of methanol and 160 g of water were charged into a 1000 ml autoclave equipped with a distillation column, and the inside of the reaction system was purged with nitrogen (pressurized to 10 kg/cm² with nitrogen). The contents of the autoclave were heated at 245° C. for 2 hr.

Subsequently, the internal pressure of the autoclave was gradually reduced and, while feeding 250 g of water over a period of 3 hr, 220 g of methanol was distilled off from the top of the distillation column provided on the autoclave. In this experiment, about 200 g of unreacted methanol was first withdrawn over a period of 20 min and, thereafter, the remaining methanol was slowly withdrawn.

Then, the autoclave was cooled to 25° C. and crystals were separated from the liquid. Thus, 98 g of NDA was recovered. The particle size distribution of the obtained NDA is given in Table 2.

The obtained NDA had its particle sizes broadly distributed from "150 µm on" to "53 µm on" and the EG slurry property thereof was as good as 3.5.

TABLE 2

|  |  | Raw material NDA | Example 2 | Example 3 |
|---|---|---|---|---|
| particle | 500 µm on | 0.3 | 0.6 | 0.4 |
| size | 300 µm on | 0.1 | 0.1 | 0.1 |
| distri- | 212 µm on | 0.1 | 1.5 | 1.2 |
| bution | 150 µm on | 0.1 | 16.3 | 10.9 |
| (wt %) | 100 µm on | 0.2 | 30.0 | 32.0 |
|  | 75 µm on | 0.1 | 13.9 | 12.6 |
|  | 53 µm on | 0.1 | 14.6 | 15.4 |
|  | 38 µm on | 0.1 | 5.3 | 7.8 |
|  | 38 µm pass | 98.9 | 17.7 | 19.6 |
| EG slurry property (EG mol/NDA mol) |  | 7 | 3.2 | 3.5 | on: particles did not pass through the sieve with the indicated opening and remained on the sieve.
pass: particles passed through the sieve with the indicated opening.

Referential Example 1

206 g of raw material NDA and 155 g of EG were charged into a glass flask provided with a simple distilling equipment, put on an 80° C. oil bath and heated to 225° C. over a period of 30 min. The slurry of NDA and EG exhibited no fluidity, so that the advance of the esterification reaction was difficult. Therefore, the operation was terminated.

Referential Example 2

206 g of raw material NDA and 248 g of EG were charged into a glass flask provided with a simple distilling equipment, put on an 80° C. oil bath and heated to 225° C. over a period of 30 min. The heating was continued at that temperature. During the heating, distillate water flowing from the top of the distillation column was recovered. The time at which the distillation of water formed as a result of the advance of the esterification was no longer observed was regarded as the completion of the esterification. 21 mg of germanium dioxide as a polymerization catalyst, and 15 mg of tetraethylammonium hydroxide and 39 mg of phosphoric acid as stabilizers were dissolved in 5 g of EG and added to the above product of esterification of NDA. The product of esterification of NDA having, added thereto, the polymerization catalyst and the stabilizers was heated to 260° C. and agitated for 1 hr while recovering distillate EG. The pressure of the reaction system was reduced to 1 Torr or below while raising the temperature thereof to 280° C. over a period of 1 hr, thereby distilling EG. The reaction was further continued for 1.5 hr at 280° C. under a reduced pressure of 1 Torr or below while distilling EG. Then, the reaction was terminated, and formed polyethylene naphthalate was recovered.

The thus recovered polyethylene naphthalate had an intrinsic viscosity of 0.54 dl/g (dissolved in a solution composed of a 1:1 mixture of o-chlorophenol and phenol and measured at 25° C.) and a Tg of 98° C. as measured by DSC. The Tm thereof could not be measured.

What is claimed is:

1. A process for producing naphthalenedicarboxylic acid particles, which comprises the steps of:

heating a liquid mixture of naphthalenedicarboxylic acid and/or an ester of naphthalenedicarboxylic acid, an alcohol and water to thereby prepare a water/alcohol solution of predetermined alcohol concentration in which naphthalenedicarboxylic acid and an ester of naphthalenedicarboxylic acid are dissolved, and lowering the alcohol concentration of the water/alcohol solution to thereby hydrolyze the ester of naphthalenedicarboxylic acid contained in the water/alcohol solution, so that naphthalenedicarboxylic acid particles are precipitated and separated.

2. The process as claimed in claim 1, wherein the liquid mixture of naphthalenedicarboxylic acid and/or an ester of naphthalenedicarboxylic acid, an alcohol and water contains the alcohol in a concentration ranging from 20 to 95% by weight based on the total of the alcohol and water.

3. The process as claimed in claim 1, wherein the alcohol concentration of the water/alcohol solution is lowered so as to range from 0 to 20% by weight based on the total of the alcohol and water.

4. The process as claimed in claim 2, wherein the alcohol concentration of the water/alcohol solution is lowered so as to range from 0 to 20% by weight based on the total of the alcohol and water.

5. The process as claimed in any one of claims 1 to 3 or 4, wherein the alcohol is methanol, ethanol or propanol.

6. The process according to any one of claims 1, 2, 3, or 5, wherein the EG slurry property value is no more than 2.5.

7. A process for producing naphthalenedicarboxylic acid particles, which comprises the steps of:

heating a liquid mixture of naphthalenedicarboxylic acid and/or an ester of naphthalenedicarboxylic acid, an alcohol and water to thereby prepare a water/alcohol solution of predetermined alcohol concentration in which naphthalenedicarboxylic acid and the ester of naphthalenedicarboxylic acid are dissolved, lowering the alcohol concentration of the water/alcohol solution to thereby hydrolyze the ester of naphthalenedicarboxylic acid contained in the water/alcohol solution, so that naphthalenedicarboxylic acid particles are precipitated, and subjecting the precipitated naphthalenedicarboxylic acid particles to a solid-liquid separation at 100° C. or higher.

8. Naphthalenedicarboxylic acid particles having an EG slurry property value of 2.7 or below, said EG slurry property value being defined as a molar ratio of ethylene glycol to naphthalenedicarboxylic acid (moles of ethylene glycol/moles of naphthalenedicarboxylic acid) of a slurry composed of a mixture of naphthalenedicarboxylic acid and ethylene glycol, said slurry having a viscosity of 1000 cP as measured by Brookfield viscometer.

9. Naphthalenedicarboxylic acid particles having an EG slurry property value of 2.7 or below, said EG slurry property value being defined as a molar ratio of ethylene glycol to naphthalenedicarboxylic acid (moles of ethylene glycol/moles of naphthalenedicarboxylic acid) of a slurry comprising a mixture of naphthalenedicarboxylic acid and ethylene glycol, said slurry having a viscosity of 1000 cP as measured by Brookfield viscometer, said naphthalenedicarboxylic acid particles comprising naphthalenedicarboxylic acid particles whose particle size is greater than 100 $\mu$m but smaller than 212 $\mu$m in a ratio of at least 50% by weight.

10. Naphthalenedicarboxylic acid particles having an EG slurry property value of 2.7 or below, said EG slurry property value being defined as a molar ratio of ethylene glycol to naphthalenedicarboxylic acid (moles of ethylene glycol/moles of naphthalenedicarboxylic acid) of a slurry comprising a mixture of naphthalenedicarboxylic acid and ethylene glycol, said slurry having a viscosity of 1000 cP as measured by Brookfield viscometer;

said naphthalenedicarboxylic acid particles comprising naphthalenedicarboxylic acid particles whose particle size is greater than 100 $\mu$m but smaller than 212 $\mu$m in a ratio of at least 50% by weight and whose particle size is smaller than 38 $\mu$m in a ratio of at least 20% by weight.

11. The naphthalenedicarboxylic acid particles according to claim 9 or claim 10, having an EG slurry property of no more than 2.5.

12. The naphthalene dicarboxylic acid particles according to claim 9, wherein from about 55 to 80 percent by weight of the particles have a particle size greater than 100 $\mu$m but smaller than 212 $\mu$m.

13. The naphthalene dicarboxylic acid particles according to claim 10, wherein from about 55 to 80 percent by weight of the particles have a particle size greater than 100 $\mu$m but smaller than 212 $\mu$m, and from 23 to 45 percent by weight of the particles have a particle size smaller than 38 $\mu$m.

* * * * *